United States Patent [19]

Taube

[11] 4,453,007

[45] Jun. 5, 1984

[54] METHOD FOR INCREASING THE PURITY OF AMPHOTERIC COMPOUND COMPOSITIONS

[75] Inventor: David Taube, Bronxville, N.Y.

[73] Assignee: USV Pharmaceutical Corporation, Tarrytown, N.Y.

[21] Appl. No.: 324,340

[22] Filed: Nov. 23, 1981

[51] Int. Cl.$^3$ .................................. C07C 149/243
[52] U.S. Cl. ........................ 562/554; 260/112.5 R; 260/239.7; 260/239.75; 260/397.7 R; 544/274; 544/275; 562/443; 562/445; 562/446; 562/450; 564/361
[58] Field of Search ............... 562/554, 557, 445, 446, 562/450; 564/344, 361; 544/273, 274, 275; 260/239.95, 239.75, 397.7 R, 397.7 D, 397.6, 112.5 R, 239.7

[56] References Cited

U.S. PATENT DOCUMENTS 3,920,737  11/1975  Horisawa .......................... 562/559

Primary Examiner—Michael L. Shippen

[57] ABSTRACT

Provided is a method of increasing the purity of amphoteric compound compositions. The method is: (a) providing an amount of a crude amphoteric compound composition, (b) using a portion of the crude composition to prepare in solution a cationic salt of the amphoteric compound, (c) using another portion of the crude composition to prepare in solution an anionic salt of the amphoteric compound, (d) mixing together the solutions wherein a precipitate is formed, and (e) collecting the precipitate which is an amphoteric compound composition of higher purity than the crude composition.

4 Claims, No Drawings

METHOD FOR INCREASING THE PURITY OF AMPHOTERIC COMPOUND COMPOSITIONS

BACKGROUND OF THE INVENTION

1. Field of the Invention

This invention relates to a method of increasing the purity of amphoteric compound compositions.

2. Prior Art

The problems concerning purification of amphoteric compound compositions are well known in the industry. These compositions, either synthesized or naturally occurring, must be purified before being used commercially.

Methods must be found which economically purify the composition to meet ever increasing standards for purity required by industry and legislation.

The present invention has discovered a method which substantially and economically improves the level of purity of amphoteric compound compositions.

SUMMARY OF THE INVENTION

The inventor has discovered a method for increasing the purity of amphoteric compound compositions containing impurities, said method comprising:

(a) providing an amount of a crude amphoteric compound composition;

(b) using a portion of the crude composition to prepare in solution a cationic salt of the amphoteric compound;

(c) using another portion of the crude composition to prepare in solution an anionic salt of the amphoteric compound;

(d) mixing together the solution containing the anionic salt and the solution containing the cationic salt, wherein a precipitate is formed; and (e) collecting the precipitate, the precipitate being amphoteric compound composition of higher purity than the crude composition.

DETAILED DESCRIPTION OF THE INVENTION

The current invention produces high purity compositions, i.e., compositions having extremely low residue on ignition. For example, when the amphoteric composition is carbocystein the level of ash on ignition is less than 0.10%.

An amphoteric compound is one which can form both anionic and cationic salts.

These compounds include amino acids, dipeptides, low molecular weight polypeptides, aminophenols, purine and sulfamide.

In particular, the method can be used to purify:

(A) Amino acids, dipeptides and other low molecular weight peptides;
  Phenigam(4-amino-3-phenylbutyric acid)
  α-methyldopa(L-2-methyl-β-(3,4-dihydroxyphenyl)alanine)
  3,5-diiodotyrosine
  Para-aminohippuric acid, and aspartame (B) Other ampholites, such as aminophenols, purines and sulfonamides;
  Terbutaline,5[2-1[(1,1-dimethyl)amino]-1-hydroxyethyl]-1,3-benzenedioxy
  Theobromine(3,7-dimethylxanthine)
  Theophylline(1,3-di-methylxanthine)
  Sulfathiazole(2-(p-aminobenzenesulfamido)-thiazole)
  Sulfadiazine(2-(p-amino-benzenesulfonamido)-pyrimidine)
  Sulfanilylurea(p-amino-benzenesulfonylurea)

"Crude amphoteric compound composition" means a composition having impurities at a higher level than it will have after being processed by the current invention. The crude composition can be naturally occurring, the product of synthesis, or can have undergone purification by another method.

The anionic salt used in the present invention has the formula $Y^+X^-$, wherein $X^-$ is an anion of the amphoteric compound and $Y^+$ is $Li^+$, $Na^+$, $K^+$, $Ca^{+2}$, $Mg^{+2}$, or $N^+[R_1, R_2, R_3, R_4]$ wherein $R_1$, $R_2$, $R_3$ and $R_4$ are independently H, lower alkyl or aryl.

The cationic salt has the formula $X^+Z^-$, wherein $X^+$ is the cation of the amphoteric compound, and $Z^-$ is an anion of an acid.

In particular $Z^-$ is $Cl^-$, $Br^-$, $I^-$, $SO_4^{-2}$, $ClO_4^-$, $RSO_3^-$ wherein R is H, lower alkyl or aryl.

The anionic salt may be prepared by making an aqueous solution containing the amphoteric compound and a salt containing the $Y^+$ ion.

The cationic salt may be prepared by making an aqueous solution containing the amphoteric compound and a salt containing the $Z^-$ ion.

After both solutions are prepared, they are mixed together. After the mixture is stirred for a time, a precipitate is formed. The precipitate is collected and washed as known to those skilled in the art. The washed precipitate is the amphoteric compound of a higher purity than the crude composition.

EXAMPLE 1

(a) Known Synthesis of Carbocysteine Crude

L-cysteine (91 kg) is dissolved in 150 liters of water. The solution is chilled and 40% sodium hydroxide solution is added portionwise so that the temperature does not rise above 18° C. The addition is stopped when a clear, dark purple solution of pH 10 is reached. Sodium monochloracetate (80 kg) is dissolved in 75 liters of water and added to L-cysteine solution. After stirring for about 1 hour, reaction mixture is charcoaled, filtered and acidified with concentrated hydrochloric acid to pH 2.5–3.0. The precipitated product is centrifuged and washed with water (2×70 liters).

(b) Known Purification Method for Carbocysteine Crude

Wet cake of SCMC crude is dissolved in sodium hydroxide solution (final pH 8) at room temperature and then precipitated with concentrated HCl (final pH 2.85), centrifuged and washed with water (7×70 liters). Yield 94–96%.

(c) New Method of Purification 17.0 g of SCMC was dissolved in 18 ml of 6 N HCl. 18.6 g of SCMC was dissolved in 102 ml of 1 N LiOH.

The two solutions were mixed at 50° C. at pH 2.2–2.8, stirred for 30 minutes with 250 ml of dionized water to obtain 33.8 g of SCMC (95%).

The purified SCMC of standard method (b) and the new method (c) were tested for ash (ROI) and monochloracetic acid (MCA) values before and after purification.

The result showed a substantially higher purity when the new method was utilized.

| A. Standard Procedure of Example 1(b) | | | |
| --- | --- | --- | --- |
| ROI(LIMIT 0.1%) | | MCA(LIMIT 0.005%) | |
| Before | After | Before | After |
| 1. 0.31 | 0.11 | 0.0423 | 0.0050 |
| 2. Not Available | 0.12 | Not Available | 0.0078 |
| 3. " | 0.12 | " | 0.0130 |
| 4. " | 0.10 | " | 0.0108 |
| 5. 0.36 | 0.13 | 0.0690 | 0.0080 |

| B. New Method of Example 1(c) | | | |
| --- | --- | --- | --- |
| ROI(Limit 0.1%) | | MCA(Limit 0.005%) | |
| Before | After | Before | After |
| 1. 0.17 | 0.000 | 0.0620 | 0.0012 |
| 2. 0.45 | 0.009 | 0.0750 | 0.0013 |
| 3. 0.31 | 0.02 | 0.0423 | 0.0013 |
| 4. Not Available | 0.03 | Not Available | 0.0010 |
| 5. 0.36 | 0.04 | 0.0690 | 0.0029 |

EXAMPLE 2

1. The solution of 35 g of SCMC in 40% $H_2SO_4$ was mixed with the water solution of SCMC potassium salt prepared from 70 g of SCMC and 22 g of KOH. The mixture was stirred, and the separated crystals were filtered and washed with deionized water until the wash gave negative sulfate $(SO_4^{-2})$ test with $BaCl_2$. The yield of dry SCMC was 100 g (95%).

| Analytical Data | |
| --- | --- |
| Residue on ignition | 0.02% |
| Monochloroacetic Acid | 12 ppm |
| $Cl^-$ | 710 ppm |
| $SO_4=$ | 240 ppm |
| $NH_4^+$ | ND |
| cysteine | ND |
| cystine | <0.1% |

EXAMPLE 3

Theobromine 18.9 g of theobromine crude was dissolved in 100 ml of 10% aqueous sodium hydroxide at 30° C. (solution A).

17.1 g of theobromine (crude was dissolved at 50° C. in 25 ml of 15% hydrochloric acid (solution B).

Solutions A and B were mixed at 50° C., stirred for 30 min., cooled to 15° C. and the product was filtered out and washed with cold water (2×25 ml).

The yield of pure theobromine was 96–98%.

I claim:

1. A method for increasing the purity of amphoteric compound compositions containing non-amphoteric impurities, said method comprising:

(a) providing an amount of a crude amphoteric compound composition;

(b) using a portion of the crude composition to prepare in solution a soluble cationic salt of the amphoteric compound having the formula $X^+Z^-$;

(c) using another portion of the crude composition to prepare in solution a soluble anionic salt of the amphoteric compound having the formula $Y^+X^-$;

(d) mixing together the solution containing the anionic salt and the solution containing the cationic salt, wherein a precipitate and a soluble salt of the formula $Y^+Z^-$ is formed; and (e) collecting the precipitate, the precipitate being amphoteric compound composition of higher purity than the crude composition, wherein the amphoteric compound is phenigam, 3,5-diiodotyrosine, para-aminohippuric acid, terbutaline, theobromine, sulfathiazole, sulfadiazin, sulfanilylurea, carbocysteine, aspartame, or methyldopa, wherein $X^+$ is the cation of the amphoteric compound, $Z^-$ is $Cl^-$, $Br^-$, $I^-$, $ClO_4^-$, or $SO_4^{-2}$;

$X^-$ is the anion of the amphoteric compound; and $Y^+$ is $Li^+$, $Ca^{+2}$, $Na^+$, $K^+$, $Mg^{+2}$, or $N^+(R_1,R_2,R_3,R_4)$;

wherein $R_1,R_2,R_3,R_4$ are H, aryl or lower alkyl.

2. A method of increasing the purity of a crude carbocysteine composition, the method comprising:

(a) dissolving a crude composition containing carbocysteine in an aqueous solution containing HCl.

(b) dissolving a crude composition containing carbocysteine in an aqueous solution containing LiOH;

(c) mixing together the solutions of steps (a) and (b); and (d) collecting the precipitate of carbocysteine.

3. The process of claim 1 wherein the amphoteric compound is carbocysteine or aspartame.

4. The process of claim 3 wherein $Y^+$ is $Li^+$ and $Z^-$ is $Cl^-$.

* * * * *